(12) United States Patent
Sijben et al.

(10) Patent No.: US 10,351,543 B2
(45) Date of Patent: Jul. 16, 2019

(54) PROCESS FOR THE PREPARATION OF A FURFURAL DERIVATIVE

(71) Applicant: Synvina C.V., Amsterdam (NL)

(72) Inventors: Johannes Maria Franciscus Sijben, Amsterdam (NL); Etienne Mazoyer, Amsterdam (NL); Ana Sofia Vagueiro De Sousa Dias, Amsterdam (NL); Gerardus Johannes Maria Gruter, Amsterdam (NL)

(73) Assignee: Synvina C.V., Amsterdam (NL)

( * ) Notice: Subject to any disclaimer, the term of this patent is extended or adjusted under 35 U.S.C. 154(b) by 0 days.

(21) Appl. No.: 15/736,033

(22) PCT Filed: Jul. 1, 2016

(86) PCT No.: PCT/NL2016/050469
§ 371 (c)(1),
(2) Date: Dec. 13, 2017

(87) PCT Pub. No.: WO2017/003293
PCT Pub. Date: Jan. 5, 2017

(65) Prior Publication Data
US 2018/0170890 A1    Jun. 21, 2018

(30) Foreign Application Priority Data
Jul. 1, 2015 (NL) .................. 2015065

(51) Int. Cl.
*C07D 307/50* (2006.01)

(52) U.S. Cl.
CPC .................. *C07D 307/50* (2013.01)

(58) Field of Classification Search
CPC .................................. C07D 307/50
USPC ....................................... 549/488
See application file for complete search history.

(56) References Cited

U.S. PATENT DOCUMENTS

| | | | |
|---|---|---|---|
| 4,740,605 A * | 4/1988 | Rapp | C07D 307/46 549/483 |
| 7,317,116 B2 | 1/2008 | Sanborn | |
| 8,242,293 B2 | 8/2012 | Gruter et al. | |
| 8,877,950 B2 | 11/2014 | Gruter et al. | |
| 2009/0131690 A1 * | 5/2009 | Gruter | C07D 307/46 549/489 |
| 2011/0082304 A1 * | 4/2011 | Gruter | C07D 307/46 549/488 |
| 2013/0324708 A1 * | 12/2013 | de Sousa Dias | C07C 67/00 536/18.6 |

FOREIGN PATENT DOCUMENTS

| | | |
|---|---|---|
| WO | 2012/091570 A1 | 7/2012 |
| WO | WO 2016207025 | * 12/2016 |
| WO | WO 2017003294 | * 1/2017 |

OTHER PUBLICATIONS

Van Putten; Chem. Rev. 2013, 113, 1499-1597. (Year: 2013).*

* cited by examiner

*Primary Examiner* — Daniel R Carcanague
(74) *Attorney, Agent, or Firm* — Hoffmann & Baron, LLP

(57) ABSTRACT

A furfural derivative having the chemical formula (1)

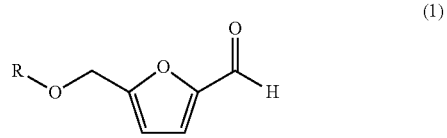

wherein R represents hydrogen, an alkyl group or an acyl group, is prepared in a process, which process includes reacting a fructose- and/or glucose-containing starting material with a liquid hydroxyl group-containing compound of formula R—OH in the presence of an acid catalyst at a reaction temperature in the range of 150 to 300° C. to produce an acid reaction mixture including the furfural derivative of chemical formula (1), which acid reaction mixture has a pH-value of smaller than 3; neutralizing the acid reaction mixture to a pH-value in the range of 3 to 6.5 to provide a partially neutralized reaction mixture; and purifying the partially neutralized reaction mixture to recover the furfural derivative of chemical formula (1).

10 Claims, No Drawings

PROCESS FOR THE PREPARATION OF A FURFURAL DERIVATIVE

CROSS-REFERENCE TO RELATED APPLICATIONS

This application is the National Stage of International Application No. PCT/NL2016/050469 filed Jul. 1, 2016, which claims the benefit of Netherlands Application No. NL 2015065, filed Jul. 1, 2015, the contents of which is incorporated by reference herein.

FIELD OF THE INVENTION

The present invention relates to a process for the preparation of a furfural derivative. The furfural derivative can be described as having the chemical formula (1):

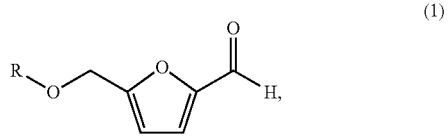

(1)

wherein R represents hydrogen, an alkyl or an acyl group.

BACKGROUND OF THE INVENTION

Furfural derivatives of chemical formula (1), including 5-hydroxymethylfurfural (HMF), 5-alkoxymethylfurfural (AlkMF) and 5-acyloxymethylfurfural (AcMF) are interesting chemicals. The furfural derivatives find application as precursor for e.g. furan dicarboxylic acid, an important monomer for polyesters, polyamides and polyurethanes. Alternatively, they can be used as fuel components. HMF has further antibacterial and anticorrosive properties. HMF, AlkMF and AcMF can be derived from sustainable sources. The furfural derivatives may be derived from a variety of carbohydrates, in particular from hexoses, such as fructose and glucose. Raw materials such as starch, cellulose, sucrose or inulin can be used as starting products for the manufacture of hexoses.

Since HMF, AlkMF and AcMF can be obtained from sustainable sources the interest in their production is growing. A process for their production is described in U.S. Pat. No. 7,317,116. This US patent specification describes a process for the preparation of HMF wherein a fructose source, such as high fructose corn syrup, and an organic solvent are heated in the presence of an acid catalyst to achieve the acid-catalyzed dehydration reaction of fructose. The resulting product may then be neutralized to a pH of 7 to 9, e.g. by the gradual addition of sodium hydroxide. In examples the neutralization is carried out to pH values of at least 7.5. Subsequently, the thus neutralized product was subjected to distillation to remove the solvent.

In a different embodiment U.S. Pat. No. 7,317,116 describes the preparation of an R'-oxymethyl furfural ether wherein R' may represent alkyl, by combining a fructose source and an R'—OH solvent and by contacting the combination thus obtained with a solid acid catalyst bed in a chromatographic column. By heating the admixture in the chromatographic column fructose is dehydrated to form R'-oxymethylfurfural ether.

In U.S. Pat. No. 8,877,950 a process is described wherein ethers of 5-hydroxymethylfurfural are manufactured by reacting a fructose-containing starting material with methanol, in the presence of a catalytic or sub-stoichiometric amount of a homogenous acid catalyst, wherein water is present as solvent in addition to the alcohol, wherein the ratio of alcohol/water-solvent is from 50:1 to 10:1, wherein the method is performed in a continuous flow process at a temperature of 175 to 225° C. and at a residence time in the flow process from 1 minute to 10 minutes. Very suitably the homogenous acid catalyst is sulfuric acid.

Further, furfural derivatives of the chemical formula (1) wherein R represents an acyl group, have been described in U.S. Pat. No. 8,242,293. Such derivatives can be prepared by reacting a fructose and/or glucose-containing starting material with a carboxylic acid in the presence of an acid catalyst in a continuous mode, wherein water is present in a small proportion. The carboxylic acid may be selected from e.g. $C_1$-$C_6$ carboxylic acids. The reaction yields esters of HMF, wherein the acyl moiety of the carboxylic acid is bonded to the oxygen atom of the oxymethyl group at the 5-position, herein referred to as AcMF. As shown in an example, sulfuric acid may be used as the acid catalyst.

The product obtained in any of these processes includes by-products, in addition to HMF and/or AlkMF and/or AcMF. A competing side reaction is the polymerization of HMF, AlkMF or AcMF and/or the hexose to form humin polymers. Humin polymers or humins are the colored bodies which are believed to be polymers containing moieties from hydroxymethylfurfural, furfural, carbohydrate and levulinic acid. Humins are obtained as insoluble solid material. As shown in the examples of U.S. Pat. No. 7,317,116, other by-products may include levulinic acid, levulinate esters and formic acid. Such by-products add to the acidity of the reaction mixture, which may already be acidic in view of the presence of the acid catalyst. It was found that under such acidic conditions degradation reactions occur which affect the yield of the desired products HMF, AlkMF and/or AcMF. Therefore, it has been proposed to neutralize the reaction mixture.

U.S. Pat. No. 7,317,116 teaches in particular a process for the preparation of HMF by i) combining a fructose source, an organic solvent, and an acid catalyst to provide a reaction mixture; ii) heating said reaction mixture to a temperature and for a time sufficient to promote a dehydration reaction of fructose in said fructose source to form a first product mixture; iii) neutralizing the pH of the first product mixture to a pH of about 7 to 9; iv) distilling the first product mixture after neutralizing the pH to remove said organic solvent remaining in the first product mixture; and v) purifying said product mixture to provide a second product mixture comprising greater than 60% by weight of HMF. In one embodiment, the product is adjusted to a neutral pH after removing the ion-exchange resin from said product mixture, and before being subjected to a distillation to remove the organic solvent.

According to U.S. Pat. No. 7,317,116 neutralization is desirable as it allows for product recovery by distillation without heat-catalyzed degradation or polymerization leading to tarry degradation products and resinous solids, i.e. humins. The neutralization step also stated to allow for product recovery with a flowing agent without such degradation or polymerization.

However, it has now been found that neutralization to alkaline pH values may still lead to degradation reactions of the desired furfural derivatives. When setting out to avoid degradation the inventors of the present invention surprisingly found that degradation reactions do not occur when the neutralization is done to a certain extent only.

SUMMARY OF THE INVENTION

Accordingly, the present invention provides a process for the preparation of a furfural derivative having the chemical formula (1)

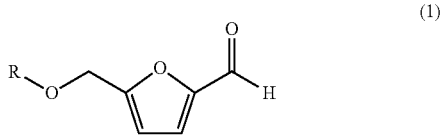

(1)

wherein R represents hydrogen, an alkyl or an acyl group, which process comprises reacting a fructose- and/or glucose-containing starting material with a liquid hydroxyl group-containing compound of formula R—OH in the presence of an acid catalyst at a reaction temperature in the range of 150 to 300° C. to produce an acid reaction mixture comprising the furfural derivative of chemical formula (1), which acid reaction mixture has a pH-value of smaller than 3;

neutralizing the pH of the acid reaction mixture to a pH-value in the range of 3 to 6.5 to provide a partially neutralized reaction mixture; and purifying the partially neutralized reaction mixture to obtain the furfural derivative of chemical formula (1).

By neutralizing to a pH value in the range of 3 to 6.5 a number of advantages are achieved. A major advantage resides in that no degradation of furfural derivatives occurs during the further steps to recover the desired furfural derivatives. Moreover, compared to the process according to U.S. Pat. No. 7,317,116, a smaller amount of neutralizing compound is needed, which not only reduces costs of the added neutralizing compounds, but also saves on effort and costs for the subsequent separation of the reaction product of the neutralizing compounds with acid components in the acid reaction mixture from the desired products.

The neutralizing of the pH of the acid reaction mixture is suitably accomplished by the addition of a neutralizing agent. Preferably, the complete product of the reaction of the fructose- and/or glucose-containing starting material with a liquid hydroxyl group-containing compound is recovered as the acid reaction mixture. However, it will be understood by the skilled person that the acid reaction mixture to be neutralized may be the major part of the reaction product when a small part of the reaction product is discharged and used for different purposes and/or when a component of the reaction product, either partially or completely, is removed before neutralization.

The neutralization of the acid reaction mixture may be complicated when the acid reaction mixture is obtained in the process for the production of the furfural derivative of chemical formula (1) wherein R is an acyl group. The liquid hydroxyl group-containing compound then represents a carboxylic acid. The presence of the carboxylic acid reactant tends to require that a significant amount of neutralizing compounds may need to be applied. Therefore, the process according to the present invention is suitably used for the preparation of furfural derivatives of chemical formula (1) wherein R represents hydrogen or an alkyl group.

DETAILED DESCRIPTION OF THE INVENTION

As apparent from the descriptions of U.S. Pat. Nos. 8,877,950 and 8,242,293 the furfural derivatives of chemical formula (1) are suitably manufactured in the presence of water. Therefore, the liquid hydroxyl-containing compound used in the present process preferably comprises water. Further, since the use of R—OH, wherein R represents hydrogen or alkyl, is preferred, suitably an alkanol, more preferably an alkanol with 1 to 6 carbon atoms is used, which alkanol optionally contains a proportion of water. Such a proportion of water may suitably range from 0.5 to 20% wt, based on the weight of the alkanol and water in the acid reaction mixture. Even more preferably, the liquid hydroxyl-containing compound comprises ethanol or methanol, most preferably methanol. As the presence of water is advantageous, the liquid hydroxyl-containing compound is suitably water, methanol or a mixture thereof.

The furfural derivative of chemical formula (1) is prepared from a reaction of a fructose- and/or glucose-containing starting material with R—OH in the presence of an acid catalyst. Suitable acid catalysts have been described in U.S. Pat. Nos. 7,317,116, 8,242,293 and 8,877,950. Such suitable catalysts include inorganic acids, such as sulfuric acid, phosphoric acid, hydrochloric acid and nitric acid, and organic acids, such as oxalic acid, levulinic acid, trifluoroacetic acid, methane sulfonic acid or p-toluene sulfonic acid. Immobilized acid catalysts in the form of e.g. sulfonic acid on resins may also be used. Other acid ion exchange resins are feasible as well as acid zeolites. Lewis acids, such as boron trifluoride or etherate complexes thereof, are further suitable catalysts. Also metals, such as Zn, Al, Cr, Ti, Th, Zr, and V can be used as catalyst in the form of ions, salts, or complexes. It appears that a wide range of acid components can be used as catalysts. The present process is very suitably carried out with an acid catalyst being a Brnsted acid selected from the group consisting of mineral inorganic acids, organic acids and mixtures thereof. Suitable mineral acids are sulfuric acid, nitric acid, hydrochloric acid and phosphoric acid, wherein sulfuric acid is particularly preferred. The organic acids are suitably selected from strong acids. Examples thereof include trifluoroacetic acid, methane sulfonic acid and p-toluene sulfonic acid.

The use of the mineral acids and strong organic acids suitably results in that the reaction mixture has a pH value of smaller than 3, preferably smaller than 2. However, it is also possible to arrive at low pH values when acid heterogeneous catalysts are used, such as acid ion exchange resins or acid zeolites. As indicated above, products of the conversion of fructose and/or glucose-containing starting materials may also include various organic acids such as levulinic acid and formic acid. The process of the present invention is therefore also suitable for embodiments wherein the reaction of the fructose and/or glucose-containing starting material is achieved with a heterogeneous, i.e. solid, catalyst.

The neutralization is suitably accomplished by the addition of a base as neutralizing agent. The base can be selected from a variety of compounds. Such compounds include those that are disclosed in the above-mentioned U.S. Pat. No. 7,317,116, such as sodium hydroxide. However, the neutralizing agent may be selected from other bases, too. The acid reaction mixture is suitably neutralized by the addition of an alkali metal or alkaline earth metal hydroxide. Other suitable bases include organic bases such as amines. Such amines include mono-, di- or trisubstituted amines. The amines may be aliphatic, cycloaliphatic or aromatic. The basic nitrogen atom of the amine may be included in the cycloaliphatic or aromatic compound or be present as an amino substituent. Suitable amines include mono-, di- and tri($C_1$-$C_4$ alkyl) amines as rather simple amino compounds. Other suitable organic bases are salts of organic oxides, such as alkoxides. Suitable alkoxides comprise alkyl moieties having from 1 to 6 carbon atoms. Examples of such alkoxides include methoxide, ethoxide, propoxide, t-butoxide and n-hexoxide salts. The counter ion is suitably selected from alkali metal and alkaline earth metal ions. However, also quaternary ammonium ions can be used. These quaternary ammonium ions may be selected from protonated amines, such as the above-mentioned amines, but also tetra-substituted quaternary ammonium ions can be used. In view of the simplicity, the ammonium ion $NH_4^+$ is the preferred ammonium ion. By neutralizing the acid reaction mixture acids are turned into salts that are to be removed from the eventual product. These salts may therefore end up in the eventual residue. Such eventual residue may comprise humin polymers. As described in U.S. Pat. No. 7,317,116 the reaction of fructose not only leads to HMF and similar products but via a competing side reaction also to humin polymers. These humin polymers, also known as humins, form a dark colored solid by-product. The salts of the neutralized acids may be separated from the product mixture together with the humins. In view of economic reasons together with the fact that hydroxides and alkoxides are easily admixed with the acid reaction mixture, the acid reaction mixture may suitably be neutralized by the addition of an alkali metal or alkaline earth metal hydroxide or alkoxide.

The neutralization is conducted to a pH value in the range of 3 to 6.5. Advantageously the neutralization is conducted to as low a pH as feasible. That implies that the pH is increased to such a low value that only a little amount of neutralizing agent is to be added to the acid reaction mixture and at the same time that the degradation of valuable products such as the furfural derivative of chemical formula (1), but also compounds such as levulinic acid and esters thereof, does not take place. It has been found that very good results are obtained when the pH is brought into the range of 3 to 6, preferably from 3 to 5, more preferably from 3 to 4.5. Such neutralization can suitably be achieved by adding an aqueous solution of the neutralizing agent to the acid reaction mixture. At the same time the skilled person will realize that it is advantageous when the neutralizing agent is added in a form as concentrated as feasible. When the neutralizing agent is added to the acid reaction mixture in the form of a concentrated solution the acid reaction solution is suitably agitated to accomplish a distribution of the neutralizing agent as quickly and as homogeneously as possible to avoid the occurrence of any side reaction between any of the products in the acid reaction mixture and the neutralizing agent.

The partially neutralized reaction mixture comprises the furfural derivative of the chemical formula (1). The furfural derivative may be recovered from the partially neutralized reaction mixture by any feasible purification step. A suitable purification step may comprise an evaporation and/or distillation step.

It has been found that in particular when the acid reaction mixture comprises an alcohol, which is especially the case when the reaction of the fructose and/or glucose-containing starting material has been conducted with a liquid hydroxyl-containing compound R—OH wherein R is an alkyl group, the carbonyl moiety in furfural derivative of chemical formula (1) obtained may react with the liquid hydroxyl group-containing compound to form a hemiacetal or acetal group. Such reaction may take place under the influence of the presence of an acid catalyst. Neutralization counteracts this acetal formation. When the partially neutralized reaction mixture comprises a sufficient amount of water, acetals formed may decompose and the furfural derivative of chemical formula (1) containing a carbonyl moiety is again obtained. Therefore, the acid reaction mixture is preferably subjected to a separation step before being neutralized wherein part of the liquid hydroxyl group-containing compound is separated from the acid reaction mixture. The remaining part of the acid reaction mixture is subsequently subjected to neutralization. When R—OH represents water it may be beneficial to remove part of the water from the acid reaction mixture before neutralization. It may lead to the formation of a more concentrated solution of the furfural derivative and other products which may facilitate their subsequent recovery. Also when the group R in the compound R—OH represents an acyl group it may be feasible to separate a part of the compounds before neutralization. In that case, some of the R—OH compounds, which are acids, can be removed to facilitate the subsequent neutralization and reduce the required amount of neutralizing agent. However, when the liquid hydroxyl group-containing compound is a compound of formula R—OH, wherein R represents an alkyl group, it is particularly advantageous to remove part of the liquid hydroxyl group-containing compound, i.e. the alcohol, before neutralization. Suitably, at least part of any water, either formed during the conversion of the fructose and/or glucose-containing starting material or already supplied together with the alcohol, in the acid reaction mixture is left in the remaining part of the acid reaction mixture. With water any acetal formed can decompose to again form the carbonyl group. Therefore the removal of alcohol is suitably carried out such that most, more preferably substantially all, alcohol is removed from the acid reaction mixture before the remainder is subjected to neutralization. A suitable method of removing the liquid hydroxyl group-containing compound is evaporation, flashing or distillation. The liquid hydroxyl group-containing compound that is recovered in this way may suitably be recycled to the reaction thereof with the fructose and/or glucose-containing starting material.

Following the neutralization step the partially neutralized reaction mixture obtained may be used to recover the furfural derivative of chemical formula (1) by purification of the partially neutralized reaction mixture. Such recovery may be conducted on the partially neutralized reaction mixture obtained. However, suitably the partially neutralized reaction mixture is subjected to separation of at least part of the liquid hydroxyl group-containing compound from the partially neutralized reaction mixture to yield a product mixture; and to recovery of the furfural derivative with the chemical formula (1) from the product mixture. In this way the reactants and the products may be obtained in a convenient way. Suitably at least part of the liquid hydroxyl group-containing compounds is removed to yield the product mixture. Such removal may include the removal of any excess R—OH that was added at the start of the reaction, but also any water that has been formed during the reaction. As indicated above it is advantageous to remove R—OH, especially in the case of R being an alkyl group, before neutralization. So for the preparation of the product mixture any remaining R—OH and water formed may suitably be removed from the partially neutralized reaction mixture. Such a removal step may suitably be carried out in the form of evaporation, flashing or distillation. Subsequently the product mixture may be used to recover the furfural derivative of chemical formula (1). The furfural derivative may be obtained by evaporation or distillation of the product mixture. When the removal step is conducted as a distillation, also other products, such as levulinic acid, levulinate esters and formic acid, may be recovered as fractions in the purification. The distillation may be carried out in one or more columns, as the skilled person will realize. The evaporation or distillation will result in a bottom residue. The bottom residue may comprise acid catalyst. It may further comprise salts that result from the neutralization of the acid reaction mixture.

Any solids that are obtained in any of the process steps are suitably removed by filtration. The solids comprise in particular humins that are the result of side-reactions of the fructose and/or glucose-containing starting material. Other solids may comprise solid salts, e.g. the salts that result from the addition of the neutralizing agent to the acid reaction mixture. Such salts may suitably comprise the alkali metal and/or alkaline earth metal salts of inorganic acids, such as sulfates, phosphates, chlorides or nitrates, when an inorganic acid is used as acid catalyst. Also such metal salts of organic acids are possible, such as alkali metal and/or alkaline earth metal salts of oxalic, p-toluene sulfonic, methane sulfonic, and trifluoroacetic acid, when such acids have been employed as acid catalyst. When a heterogeneous catalyst has been used, solid salts of products such as levulinic acid or formic acid may be formed. Solids removal is suitably carried out by filtration of the acid reaction mixture. In this way the filtrate of the acid reaction mixture is a homogenous liquid which facilitates handling, such as stirring during the neutralization. The filtered solids, such as humins, are suitably washed with water to remove acid catalyst, if any. Washing can suitably be done with water. In an alternative embodiment, the solids are separated by means of centrifugation.

Alternatively, the solids removal, e.g. filtration or centrifugation, is carried out after neutralization at the partially neutralized reaction mixture. Due to the neutralization, some solid salts may have been formed. Such salts are then suitably removed together with the humins fraction. If desired, the partially neutralized reaction mixture may be subjected to an evaporation step to remove at least some of the water and, optionally, alcohol or other volatile components, in order to concentrate the products and the solids so that most, if not all, of the salts formed are precipitated and removed together with the humins.

When the furfural derivative of chemical formula (1) is recovered by evaporation or distillation the bottom residue may comprise any remaining acid catalyst and/or dissolved salts resulting from the neutralization. The bottom residue is suitably treated to remove as much acid catalyst and as much salt as possible so that the remaining treated residue can be either combusted or discharged in another environmentally-friendly way. Thereto, the bottom residue is preferably washed with an aqueous liquid. Thereby water-soluble salts and acid are suitably removed from the residue.

The fructose- or glucose-containing starting material may be selected from a variety of possible feedstocks. The starting material may comprise mono-, di-, oligo- or polysaccharides. The components of particular interest in biomass are those feedstocks that contain a monosaccharide. Examples of suitable monosaccharides include fructose and mixtures of fructose with other monosaccharides, such as other hexoses and/or pentoses. Suitable other hexoses include but are not limited to glucose, galactose, mannose, and their oxidized derivatives, e.g. aldonic acid, reduced derivatives, e.g. alditol, etherified, esterified and amidated derivatives. The di- and oligosaccharide carbohydrates containing more than one saccharide unit, are suitably hydrolysed in the alcohol, resulting in a mixture of dissolved di- and/or oligosaccharides, monomeric saccharide units and/or glycoside units. Examples of suitable disaccharides include maltose, lactose, trehalose, turanose and sucrose, sucrose being preferred. Sucrose is abundantly available and therefore very suitable. The disaccharides can easily be converted into the monomeric units. Examples of suitable oligosaccharide are fructo-oligosaccharides which are found in many vegetables. By oligosaccharides is understood a carbohydrate that is built up of 3 to 10 monosaccharide units. Polysaccharides have more than ten monosaccharide units. These are polymeric structures formed of repeating units joined together by glycosidic bonds. The number of monosaccharide units in a polysaccharide may vary widely, and may range from 10 to 3000. Suitable polysaccharides include fructan, i.e. a polymer of fructose moieties, and levan, which is composed of D-fructofuranosyl moieties. Mixtures may also be used. Hydrolysis process streams from enzymatic or catalytic hydrolysis of starch, cellulose and hemi-cellulose or from alcoholysis processes that already contain mono- and disaccharides can suitably be used as starting material for the present process. In view of the above, the preferred monosaccharide is fructose, glucose and mixtures thereof. A suitable starting material is HFCS, i.e. high fructose corn syrup, comprising a major amount of fructose and some glucose. The preferred disaccharide is sucrose.

The fructose and/or glucose starting material may further comprise glycosides as described in WO 2012/091570.

The conditions under which the present process can be carried out has been generally described in the prior art. Advantageously, the process is carried out as described in U.S. Pat. No. 8,877,950. For the reaction between the fructose and/or glucose-containing starting material with the compound R—OH that includes preferably a temperature of 175 to 225° C. and at a residence time in the flow process from 1 minute to 10 minutes. The pressure is preferably in the range of 5 to 100 bar, more preferably from 10 to 40 bar. The process is preferably carried out as a continuous process. The conditions for the neutralization are not critical. The pressure has little influence on the reaction. Therefore, the pressure may vary between wide ranges at the discretion of the skilled person. Suitable pressures include those in the range of 0.1 to 40 bar. Also the temperature for the neutralization may be selected from a wide range and is suitably selected such that the at least part of the acid reaction mixture is neutralized at a temperature in the range of 25 to 150° C.

The present invention will be illustrated by means of the following example.

EXAMPLE

To mimic a reaction product of the reaction described in U.S. Pat. No. 8,877,950 wherein the methyl ether of 5-hydroxymethylfurfural is manufactured by reacting a fructose-containing starting material with methanol in the presence of sulfuric acid as a homogenous acid catalyst, a composition comprising methoxymethylfurfural (MMF), methyl levulinate (ML), hydroxymethylfurfural (HMF), water, methanol, sulfuric acid, levulinic acid and formic acid was prepared. The pH of the composition was below 2.5. The amounts of the desired products MMF, HMF and ML were determined. In one experiment (Exp. No. 1) a portion of the composition was refluxed for 1 hour, and volatile compounds, such as methanol, were removed at 60° C. under reduced pressure to mimic the recovery of MMF and HMF. The resulting amounts of MMF, HMF and ML in the remaining liquid were again determined.

In three other experiments (Exp. Nos. 2 to 4), three identical portions of the composition were partially neutralized at ambient conditions by addition of aqueous sodium hydroxide under vigorous stirring to reach different pH values. In the Table below the pH values obtained after the addition of the sodium hydroxide solutions are indicated. The different partially neutralized reaction mixtures thus obtained were also refluxed for 1 hour, and volatile compounds, such as methanol, were removed at 60° C. under reduced pressure to mimic the recovery of MMF and HMF. In each of the mixtures the amounts of MMF, HMF and ML of the remaining liquids were determined.

The relative reduction of the products MMF, HMF and ML in the four resulting mixtures were determined. The results are shown in the Table below. The numbers indicate the proportion of the product, expressed in mol %, which had disappeared after the period of refluxing and volatiles removal.

TABLE

Reduction of products MMF, HMF and ML after reflux and volatiles removal

| Experiment No. | pH | MMF, mol % | HMF, mol % | ML, mol % |
|---|---|---|---|---|
| 1 | <2.5 | 7 | 15 | 20 |
| 2 | 4.2 | 0 | 0 | 0 |
| 3 | 5.0 | 0 | 0 | 0 |
| 4 | 7.0 | 0 | 0 | 0 |

The results show that neutralization does not need to be complete to avoid the degradation of MMF, HMF and ML. By only partially reducing the acid reaction mixture, their degradation is avoided and at the same time the required amount of neutralizing agent is reduced.

The invention claimed is:

1. A process for the preparation of a furfural derivative having the chemical formula (1)

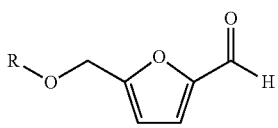

(1)

wherein R represents hydrogen, an alkyl group or an acyl group, which process comprises:
reacting a fructose- and/or glucose-containing starting material with a liquid hydroxyl group-containing compound of formula R—OH in the presence of an acid catalyst at a reaction temperature in the range of 150 to 300° C. to produce an acid reaction mixture comprising the furfural derivative of chemical formula (1), which acid reaction mixture has a pH-value of smaller than 3;
neutralizing the acid reaction mixture to a pH-value in the range of 3 to 6.5 to provide a partially neutralized reaction mixture; and
purifying the partially neutralized reaction mixture to recover the furfural derivative of chemical formula (1), wherein, if R represents an acyl group, the acyl group is derived from a carboxylic acid that is selected from $C_1$-$C_6$ carboxylic acids, and
wherein the acid reaction mixture has a pH of smaller than 2.

2. The process according to claim 1, wherein the liquid hydroxyl group-containing compound is water or methanol or a mixture thereof.

3. The process according to claim 1, wherein the acid catalyst is a Brnsted acid selected from the group consisting of mineral inorganic acids, organic acids and mixtures thereof.

4. The process according to claim 1, wherein the acid reaction mixture is neutralized by the addition of an alkali metal or alkaline earth metal hydroxide or alkoxide.

5. The process according to claim 1, wherein the acid reaction mixture is subjected to a separation step before being neutralized wherein part of the liquid hydroxyl group-containing compound is separated from the acid reaction mixture.

6. The process according to claim 5, wherein the partially neutralized reaction mixture is subjected to separation of at least part of the liquid hydroxyl group-containing compound from the partially neutralized reaction mixture to yield a product mixture; and to recovery of the furfural derivative with the chemical formula (1) from the product mixture.

7. The process according to claim 6, wherein the partially neutralized reaction mixture is subjected to evaporation to yield the product mixture.

8. The process according to claim 1, wherein the furfural derivative with the chemical formula (1) is recovered by evaporation or distillation to yield the furfural derivative with the chemical formula (1) and a bottom residue comprising acid catalyst.

9. The process according to claim 8, wherein the bottom residue is washed with an aqueous liquid.

10. The process according to claim 1, wherein the acid reaction mixture is neutralized at a temperature in the range of 25 to 150° C. and a pressure of 0.1 to 40 bar.

* * * * *